United States Patent [19]

Lavender et al.

[11] Patent Number: 5,080,661
[45] Date of Patent: Jan. 14, 1992

[54] FIXATION PIN ENTRY SITE DRESSING AND METHOD

[75] Inventors: Michael R. Lavender, Round Lake Beach; James A. Stupar, Crystal Lake, both of Ill.

[73] Assignee: Hollister Incorporated, Libertyville, Ill.

[21] Appl. No.: 686,391

[22] Filed: Apr. 18, 1991

[51] Int. Cl.⁵ ............................................. A61F 13/00
[52] U.S. Cl. ....................................... 606/54; 606/53; 128/888
[58] Field of Search .................... 606/53, 54; 604/192, 604/198; 128/884, 887, 888

[56] References Cited

U.S. PATENT DOCUMENTS

| | | | |
|---|---|---|---|
| 2,221,758 | 11/1940 | Elmquist | 128/888 |
| 2,346,346 | 4/1944 | Anderson | 128/92 |
| 2,362,741 | 11/1944 | Berke | 606/54 |
| 3,234,941 | 2/1966 | Tucker | 128/888 |
| 3,270,743 | 9/1966 | Gingras | 604/192 |
| 3,334,626 | 8/1967 | Schimmel | 128/888 |
| 3,528,416 | 9/1970 | Chamberlain | 128/888 |
| 3,782,377 | 1/1974 | Rychlik | 128/888 |
| 4,040,427 | 8/1977 | Winnie | 128/348 |
| 4,535,763 | 8/1985 | Jaquet | 128/92 A |
| 4,755,170 | 7/1988 | Golden | 604/192 |
| 4,856,504 | 8/1989 | Yamamoto et al. | 128/92 ZW |
| 4,915,694 | 4/1990 | Yamamoto et al. | 604/180 |
| 4,920,959 | 5/1990 | Witzel | 606/53 |
| 4,988,341 | 1/1991 | Columbus et al. | 128/888 X |
| 4,998,935 | 3/1991 | Pennig | 606/54 |

FOREIGN PATENT DOCUMENTS 2215214  9/1989  United Kingdom .

OTHER PUBLICATIONS (Advertising Sheet) "Introducing the AME PinSite Shield," by American Medical Electronics, Inc. (copyrighted 1989).

Primary Examiner—Robert A. Hafer
Assistant Examiner—Sam Rimell
Attorney, Agent, or Firm—Tilton, Fallon, Lungmus

[57] ABSTRACT

An external fixation pin entry site dressing, and the method of its application, in which an elongate body of soft, tearable, and compressible absorbent material has a longitudinal primary slit extending inwardly from one side of the body to about the longitudinal midline thereof and a plurality of pairs of transverse slits extending inwardly from opposite sides of the body and partially dividing the body into a multiplicity of separable segments. A user compares the length of a portion of a fixation pin, exposed between a mounting bracket and the skin at the entry point for the pin, with the thickness of one or more of the segments while the dressing is in an uncompressed condition, tears the dressing apart along one of the central septa connecting adjacent segments to separate from the block one or more segments having a total thickness in an uncompressed state greater than the exposed length of fixation pin, and then compresses the separated segment(s) and fits such separated segment(s) onto the fixation pin with the portion of the pin between the bracket and the skin being received in the primary slit.

13 Claims, 1 Drawing Sheet

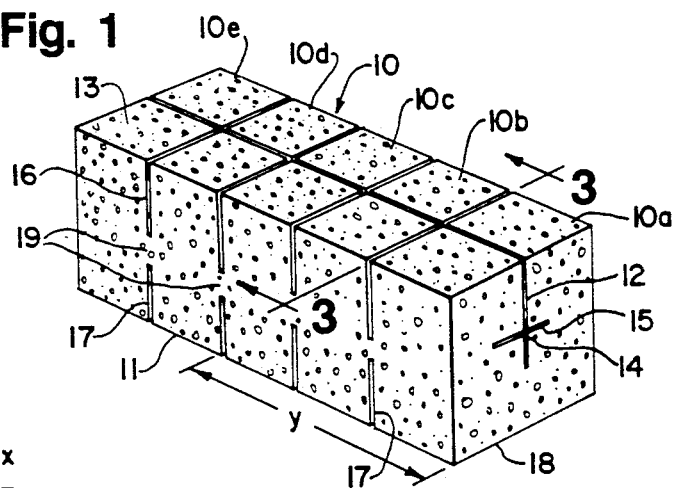
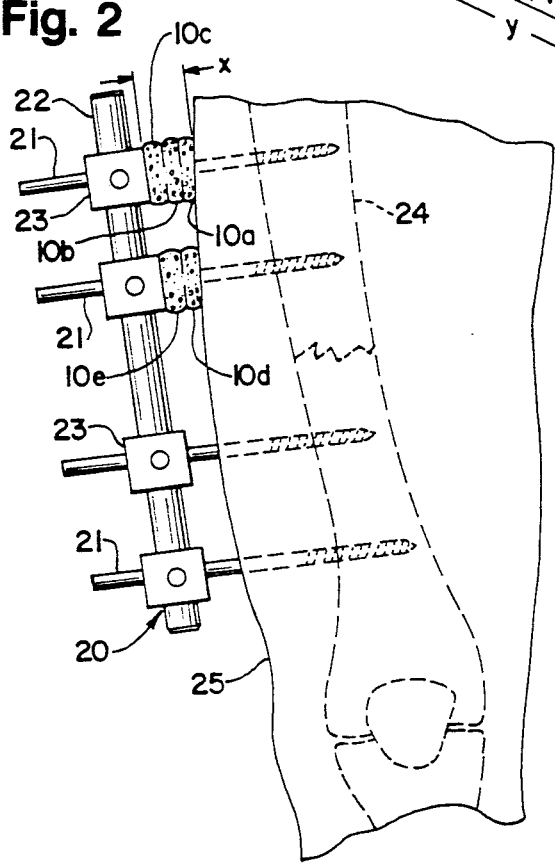
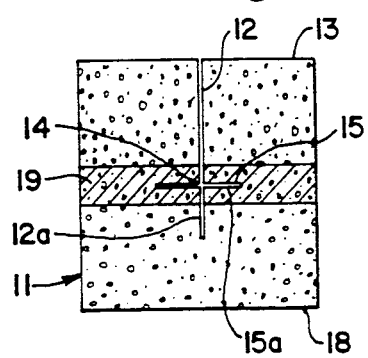
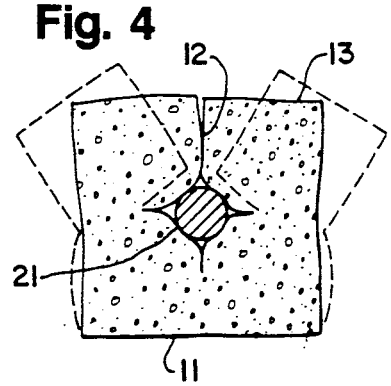
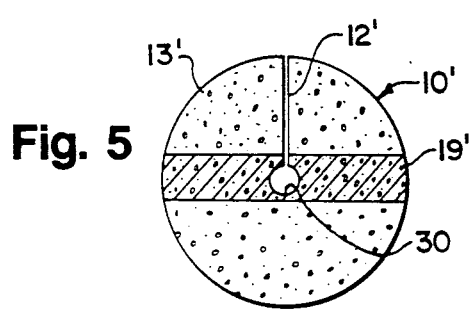

FIXATION PIN ENTRY SITE DRESSING AND METHOD

BACKGROUND AND SUMMARY

External fixation systems for use in repairing bone fractures are well known and are disclosed, for example, in U.S. Pat. Nos. 2,346,346, 4,535,763, and 4,920,959. Their purpose is to orient and immobilize sections of a fractured bone during a period of osteogenesis and healing. Such a system necessarily involves the use of fixation pins that are extended through the patient's skin into the bone sections requiring alignment and immobilization. Maintaining the pin entry points through the skin clean and free of infection are major objectives in the use of any external fixation system. At the same time, a dressing designed for that purpose must be readily removable, replaceable, and simple to apply in an effective manner regardless of differences in the length of fixation pins exposed between the entry slits and the mounting brackets of the device.

Pin-site shields or dressings are available which take the form of foam discs associated with attachment means such as clamping rings or clips. In one such construction, a foam disc is lined on one side with fabric and has its opposite side secured to a rigid plastic disc equipped with a set screw. A radial slit in the disc allows it to be fitted onto a fixation pin and, by tightening the set screw, the disc is then locked in place against the skin at the entry site. Such a device tends to be awkward to operate and lacks automatic means for exerting a controlled amount of dressing pressure at the wound site. Depending on just where the user tightens the set screw against the fixation pin, the force applied by the dressing against the wound site might be excessive, insufficient, or totally lacking. Furthermore, the complexity of such a two-piece construction—with one of the elements performing a dressing function and the other an attachment function—renders the device relatively expensive for a user who may, at least in some cases, be required to change the dressings at multiple sites two or more times a day.

Accordingly, an important aspect of this invention lies in providing a simple and inexpensive fixation pin entry site dressing, and its method of use, in which both the attachment and absorptive functions are performed by the same unitary element. Another important objective is to provide a dressing that may be quickly sized to suit the reception site and easily applied or removed from that site. Despite its ease of removability when wound inspection or dressing replacement is desired, the dressing is self-retentive and notably effective at remaining in place until removal is required. The dressing of this invention has been found particularly effective at absorbing exudate for preventing skin maceration, covering a pin site while at the time maintaining an open pathway to allow fluid to escape, protecting clothing and linens from exudate contact, and stabilizing the skin relative to a fixation pin, thereby preventing relative skin movement that could result in inflammation and predispose the site to infection.

In brief, the external fixation pin dressing of this invention takes the form of an elongate block of soft, compressible, liquid-absorbent material capable of being torn apart at any of a number of predetermined zones of separation with little or no fragmentation or free particle release. The block is composed of a multiplicity of connected segments, each segment being partially separated from adjacent segments by pairs of transverse slits extending inwardly from opposite sides of the block. A connecting septum joins each segment to an adjacent segment and each septum is tearable for disconnecting one segment, or a selected number of joined segments, from the remainder of the block.

In addition, the block is provided with a longitudinally extending primary slit that extends inwardly from one side of the block and, in a preferred embodiment, a longitudinal cross slit within the block that intersects the primary slit along the block's longitudinal mid-line. In applying a dressing, a user simply removes a selected number of segments from the block (the total length of the selected segment(s) being greater, when the foam is uncompressed, than the exposed length of fixation pin to be covered), then longitudinally compresses the selected segment(s) and fits it onto the exposed shaft of the pin immediately adjacent the entry site. When the dressing is properly in place, the pin extends through the dressing segment(s) along the intersection of the primary slit and the longitudinal cross slit. Since the applied dressing remains in a state of compression after being fitted about the shaft of the pin, it stabilizes itself in place and in firm contact with the skin surface surrounding the pin entry site, thereby accomplishing the objectives of covering the pin site and stabilizing the skin around that site.

Other features, advantages, and objects of the invention will become apparent from the specification and drawings.

DRAWINGS

FIG. 1 is a perspective view of a dressing block embodying the invention.

FIG. 2 is a fragmentary view depicting the dressing in use with an external fixation pin system.

FIG. 3 is a cross sectional view taken along line 3—3 of FIG. 1.

FIG. 4 is an end view of an applied dressing showing the relationship of the dressing and a fixation pin extending therethrough.

FIG. 5 is a cross sectional view similar to the view of FIG. 3 but showing an alternate embodiment of the invention.

DETAILED DESCRIPTION OF PREFERRED EMBODIMENT

FIG. 1 depicts dressing 10 in the condition it would be supplied to users, it being understood, of course, that the dressing would be supplied in sterile form and that a protective wrapper or envelope has been removed to expose the dressing. In general, the dressing takes the form of an elongate block or body 11 of generally uniform cross section. A square cross sectional configuration is preferred because the edges make it easier for a user to grip and manipulate the dressing segments when application to a pin entry site is desired; however, it is to be understood that other cross sectional configurations may be used and, if desired, the body 11 may even be cylindrical in shape (as indicated in FIG. 5).

A longitudinal primary slit 12 extends inwardly from one side 13 of the body and, in the embodiment of FIGS. 1-4, terminates inwardly well beyond the longitudinal midline 14 of the body. A longitudinal cross slit 15 intersects the primary slit 12 along the longitudinal midline of the body and, as shown most clearly in FIG. 3, is disposed at right angles to the primary slit. The legs 15a of the cross slit on opposite sides of the primary slit are of equal length and preferably are of substantially the same length as the leg 12a of the primary slit extending beyond cross slit 15.

The body also includes a plurality of pairs of transverse slits 16, 17 extending inwardly from opposite sides 13, 18 of the body. The pairs of transverse slits partially divide the body into a multiplicity of dressing segments 10a, 10b, 10c, 10d, and 10e. Each segment is connected to an adjacent segment by an integral septum 19 disposed between the opposing transverse slits 16, 17 of each pair. While a body 10 having five such segments is depicted in FIG. 1, it is to be understood that different numbers may be provided but that, in general, the segments should be three or more in number if the full benefits of this invention are to be realized. All of the segments are shown to be of uniform thickness; while that is preferred, such segments also might possibly be arranged in a series of different selected thicknesses.

The absorbent material of the dressing is not only soft and compressible but is also weak enough to permit a user to separate one or more segments from the remainder of the block when application of a dressing is desired. The tearing occurs along a selected septum 19. One or more segments are simply pulled away from the remainder of the block by tearing the septum connecting the two.

The number of segments to be torn away as a group is determined by the length of that portion of the fixation pin extending between a pin-mounting bracket and the patient's skin surface at the entry site. Referring to FIG. 2, for example, the numeral 20 generally designates an external fixation system having a plurality of fixation pins secured to a rigid frame or bar 22 by means of adjustable brackets 23. The pins are threaded into sections of a fractured bone 24 to orient and immobilize those sections. It is the portion of each pin 21 extending between surface 25 and pin-mounting bracket 23 that is to be surrounded by the pin site dressing. To that end, the user estimates the length x of the portion of each pin between the skin and the bracket and compares that length with dressing block 10 to select the number of segments that in uncompressed condition will exceed length x by a distance not exceeding the thickness of one segment. In the example shown at the top of FIG. 2, three segments of total length y are required to exceed length x. Therefore, a user simply separates a combined group of segments 10a, 10b, 10c from the remainder of the block, by tearing the septum 19 between segments 10c and 10d, and then axially compresses the group of three segments and fits them onto the fixation pin with the portion of the pin between the skin and bracket being received through slit 12 and extending along the intersection 14 between longitudinal slits 12 and 15 (FIG. 4). The corners of the absorbent material at the intersection are readily compressed outwardly to accommodate pin 21, allowing slit 12 to become closed or substantially closed. The dressing, when fitted into place and released, remains in a state of limited longitudinal compression.

Depending on the length of pin exposed between its bracket and the skin surface, the applied dressing may take the form of one segment or any selected number of joined segments. It will be noted, therefore, that only two connected segments are fitted onto the second pin from the top in FIG. 2. The lower pins are shown without dressings applied; in use of the invention, such pins would also be covered in the manner described and illustrated.

The pin site dressing of this invention may be fabricated of any suitable material that is soft, highly absorbent, resilient, hydrophilic, and capable of being torn apart at the connecting septa 19 without fragmenting. It is believed that various materials might be selected to meet such requirements including, for example, fibrous or felted materials that are porous, highly-absorbent, compressible and recoverable, and treated so that they are not only hydrophilic but do not disintegrate or release fibrous particles when adjacent segments are separated or when such material is compressed and allowed to expand. Soft, resilient, open-cell, hydrophilic polymeric foam materials (especially such materials that have been compacted or "felted" as that term is commonly used, to reduce pore size, increase pore density, and increase absorbency) have been found suitable. Particularly effective results have been obtained using a felted polyurethane foam commercially treated during manufacture with a surfactant to promote hydrophilicity. Prior to felting, such a foam may, for example, have a density of about 2 pounds per cubic foot; compaction in a commercial felting process may increase that to 6 pounds per cubic foot and produce a foam which is capable of holding far more than 30 times its weight of water.

The use of polymeric foam is particularly advantageous because during manufacture the dressing may be cut, and the slits may be formed, without producing fragments, using various well-known cutting techniques. Also, the segments may be pulled apart, rupturing the septa that connect them, with little or no fragmentation. Thus, the possibilities of dressing fragments being released at the pin entry site are substantially if not completely eliminated.

The dressing is not only absorbent and maintains an open pathway for allowing fluid to escape from the pin site but, because of its resilience, stabilizes the contacted skin in relation to the pin, thereby preventing skin movement that might result in inflammation and a predisposition to infection. Moreover, the expansive force exerted by the dressing when it is in a state of moderate compression between the skin surface 25 and bracket 23 renders the dressing self-retaining in use. The need for providing separate attachment means is therefore eliminated.

The embodiment of FIG. 5 is identical to that of FIGS. 1-4 except that dressing 10' is cylindrical (circular rather than square in cross section) and is provided with a central opening 30 rather than a cross slit. The opening is smaller in diameter than the external diameter of the fixation pin upon which the dressing is intended to be fitted. Septa 19' connect adjacent segments in the same manner as described with respect to septa 19, and the materials involved, and the procedure for using dressing 10', are the same as already described. While this embodiment may have an advantage of helping to insure that slit 12' will be completely closed as arms 13' wrap about a pin extending through opening 30, it may also have a disadvantage of greater manufacturing/purchasing cost.

In both embodiments, the dressings may be made available to the user in a dry state or may be impregnated or coated with suitable fluids that enhance their use. Thus, the dressings may be impregnated with an antibiotic agent, either in a liquid or dry state, or they may contain a sterile lubricant that prevents the dressings from sticking to fixation pins when dressing removal is desired.

While in the foregoing we have disclosed embodiments of the invention in considerable detail for purposes of illustration, it will be understood by those skilled in the art that many of these details may be varied without departing from the spirit and scope of the invention.

We claim:

1. An external fixation pin site dressing comprising an elongate body of soft, compressible, resilient and highly-absorbent material having a longitudinal primary slit extending inwardly from one side of said body; and a plurality of pairs of transverse slits extending inwardly from opposite sides of said body and partially dividing said body into a multiplicity of segments; said transverse slits of each pair being coplanar and having inner edges spaced apart to define a narrow connecting septum between adjacent segments; each septum providing a tearable connection between adjacent segments permitting separation of a single segment, or a selected number of joined segments, from the remainder of said body so that said separated segment or segments may be longitudinally compressed and fitted onto a portion of a fixation pin extending between a patient's skin and a fixation pin bracket with such pin portion being fully received in said longitudinal primary slit.

2. The dressing of claim 1 in which all of said segments are of substantially equal thickness.

3. The dressing of claims 1 or 2 in which said body is of generally uniform rectangular cross section with substantially planar sides.

4. The dressing of claim 3 in which said primary slit extends outwardly to one side of said dressing.

5. The dressing of claims 1 or 2 in which said body is cylindrical in shape.

6. The dressing of claim 1 in which said body also has a longitudinal cross slit intersecting said primary slit along said body's longitudinal midline; said cross slit being disposed at right angles to said primary slit and bisected by said primary slit.

7. The dressing of claim 1 in which each septum extends in a direction normal to the plane of said primary slit.

8. The dressing of claim 1 in which said body is formed of a soft, resilient, open-cell, hydrophilic foam.

9. The dressing of claim 8 in which said foam is polyurethane foam.

10. The dressing of claims 1 or 2 in which said body is impregnated with a medical treatment agent.

11. A method of dressing the entry site for a fixation pin extending from a mounting bracket through the surface of a patient's skin and into a bone therebeneath, comprising the steps of providing a block of soft, compressible, resilient and highly-absorbent material having a longitudinal primary slit extending along the block's longitudinal midline and a plurality of pairs of transverse slits extending inwardly from opposite sides of said block and partially dividing said block into a multiplicity of segments connected in series by narrow integral septa; comparing the distance between said mounting bracket and a patient's skin with a thickness of one or more of said uncompressed segments; tearing a septum to separate from said block one or more segments having a total thickness in an uncompressed state greater than said distance; then longitudinally compressing said one or more separated segments to a thickness less than said distance; fitting said one or more separated segments, while compressed, onto said fixation pin with the portion of said pin between said bracket and said skin being received in said primary slit; and relieving the compressive force to allow said one or more segments to expand longitudinally into contact with said bracket and said skin.

12. The method of claim 11 in which said dressing also has a longitudinal cross slit intersecting said primary slit along the block's longitudinal midline; said step of fitting said one or more segments onto a fixation pin including advancing said one or more segments until said pin is located at the intersection of said primary slit and said cross slit.

13. The method of claim 11 in which said segments are of uniform thickness and said tearing step includes tearing a septum to separate from said block one or more segments having a total thickness in an uncompressed state that is greater than said distance by an extent not exceeding the thickness of one of said segments.

* * * * *